(12) United States Patent
Bailey, Jr.

(10) Patent No.: US 12,398,889 B1
(45) Date of Patent: Aug. 26, 2025

(54) FURNACE SHUT OFF DEVICE

(71) Applicant: James E Bailey, Jr., Reedville, VA (US)

(72) Inventor: James E Bailey, Jr., Reedville, VA (US)

( * ) Notice: Subject to any disclaimer, the term of this patent is extended or adjusted under 35 U.S.C. 154(b) by 485 days.

(21) Appl. No.: 17/962,693

(22) Filed: Oct. 10, 2022

(51) Int. Cl.
| F24D 19/10 | (2006.01) |
| F23N 5/24 | (2006.01) |
| G01N 33/00 | (2006.01) |

(52) U.S. Cl.
CPC ............. *F24D 19/10* (2013.01); *F23N 5/242* (2013.01); *G01N 33/0063* (2013.01); *F23N 2231/22* (2020.01)

(58) Field of Classification Search
None
See application file for complete search history.

(56) References Cited

U.S. PATENT DOCUMENTS

| 5,896,089 | A | | 4/1999 | Bowles | |
| 6,989,757 | B2 * | | 1/2006 | Geoffrey J. | ............ G08B 25/14 |
| | | | | | 340/506 |
| 2013/0157559 | A1 * | | 6/2013 | Flammer, III | ......... G08B 21/12 |
| | | | | | 455/7 |
| 2017/0261214 | A1 * | | 9/2017 | Lai | ........................... H04L 12/00 |
| 2019/0221101 | A1 * | | 7/2019 | Golob | ..................... H04W 4/80 |
| 2019/0226595 | A1 * | | 7/2019 | Mattos | ...................... F17D 5/06 |
| 2019/0378399 | A1 * | | 12/2019 | Hoofe, IV | ............. G08B 25/10 |
| 2020/0372768 | A1 * | | 11/2020 | Armpriester | ........... G08B 21/02 |
| 2021/0145703 | A1 * | | 5/2021 | Sjöö | ........................ A61Q 19/00 |
| 2021/0180235 | A1 * | | 6/2021 | Gnadeberg | .............. D06F 33/37 |
| 2021/0222877 | A1 * | | 7/2021 | Combe | ................ G08B 21/182 |
| 2021/0349066 | A1 * | | 11/2021 | Chilla | ..................... G08B 21/14 |
| 2021/0407280 | A1 * | | 12/2021 | Hoofe, IV | ........... G08B 25/016 |
| 2022/0027725 | A1 * | | 1/2022 | Nongpiur | ................. G06N 7/01 |
| 2022/0043412 | A1 * | | 2/2022 | Dedul | ................... F24D 11/005 |

* cited by examiner

*Primary Examiner* — Ko-Wei Lin
(74) *Attorney, Agent, or Firm* — Sanchelima & Associates, P.A.; Jesus Sanchelima; Christian Sanchelima

(57) ABSTRACT

A furnace shut off device including a sensor assembly, a shutoff assembly and an alarm assembly. The sensor assembly includes a plurality of sensors. The plurality of sensors can be used to collect data of carbon monoxide concentration level. The shutoff assembly includes a microcontroller. The microcontroller receives the collected data from the plurality of sensors to shut off a furnace unit if the carbon monoxide concentration level is high. The alarm assembly includes a display, a light and a speaker. The microcontroller actuates said display, said light and said speaker if the carbon monoxide concentration level is high.

11 Claims, 3 Drawing Sheets

FURNACE SHUT OFF DEVICE

BACKGROUND OF THE INVENTION

1. Field of the Invention

The present invention relates to a furnace shut off device and, more particularly, to a furnace shut off device that can automatically shut off a furnace unit if a dangerous level of carbon monoxide (CO) is detected.

2. Description of the Related Art

Several designs for shut off devices have been designed in the past. None of them, however, include a transmitter to send an alarm to a mobile device when dangerous CO levels are detected.

Applicant believes that a related reference corresponds to U.S. Pat. No. 6,989,757 issued for a proactive carbon monoxide monitoring, alarm and protection system that is adapted to turn off the source of carbon monoxide, sound a central alarm, and alert an off-site monitoring station upon detection of carbon monoxide by the detector. Applicant believes that another related reference corresponds to U.S. Pat. No. 5,896,089 issued for a dual carbon monoxide detection system with gas cut off and alarm capabilities. None of these references, however, teach of a furnace safety device comprising multiple carbon monoxide sensors connected to an alarm system and an automatic shut off device, such that if the sensors measure an elevated or dangerous level of CO in the residence, the system will emit alarms and shut down the furnace.

Other documents describing the closest subject matter provide for a number of more or less complicated features that fail to solve the problem in an efficient and economical way. None of these patents suggest the novel features of the present invention.

SUMMARY OF THE INVENTION

It is one of the objects of the present invention to provide a furnace shut off device that includes a speaker suitable to emit an audible sound to prevent the user of high CO levels.

It is another object of this invention to provide a furnace shut off device that includes a display to show the current CO level and prevent if that level is dangerous, the display may also display if the sensors are working adequately.

It is still another object of the present invention to provide a furnace shut off device that includes a microcontroller suitable to control the shut off of a furnace unit if the CO levels are high.

It is yet another object of this invention to provide such a device that is inexpensive to implement and maintain while retaining its effectiveness.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

Figure 1:
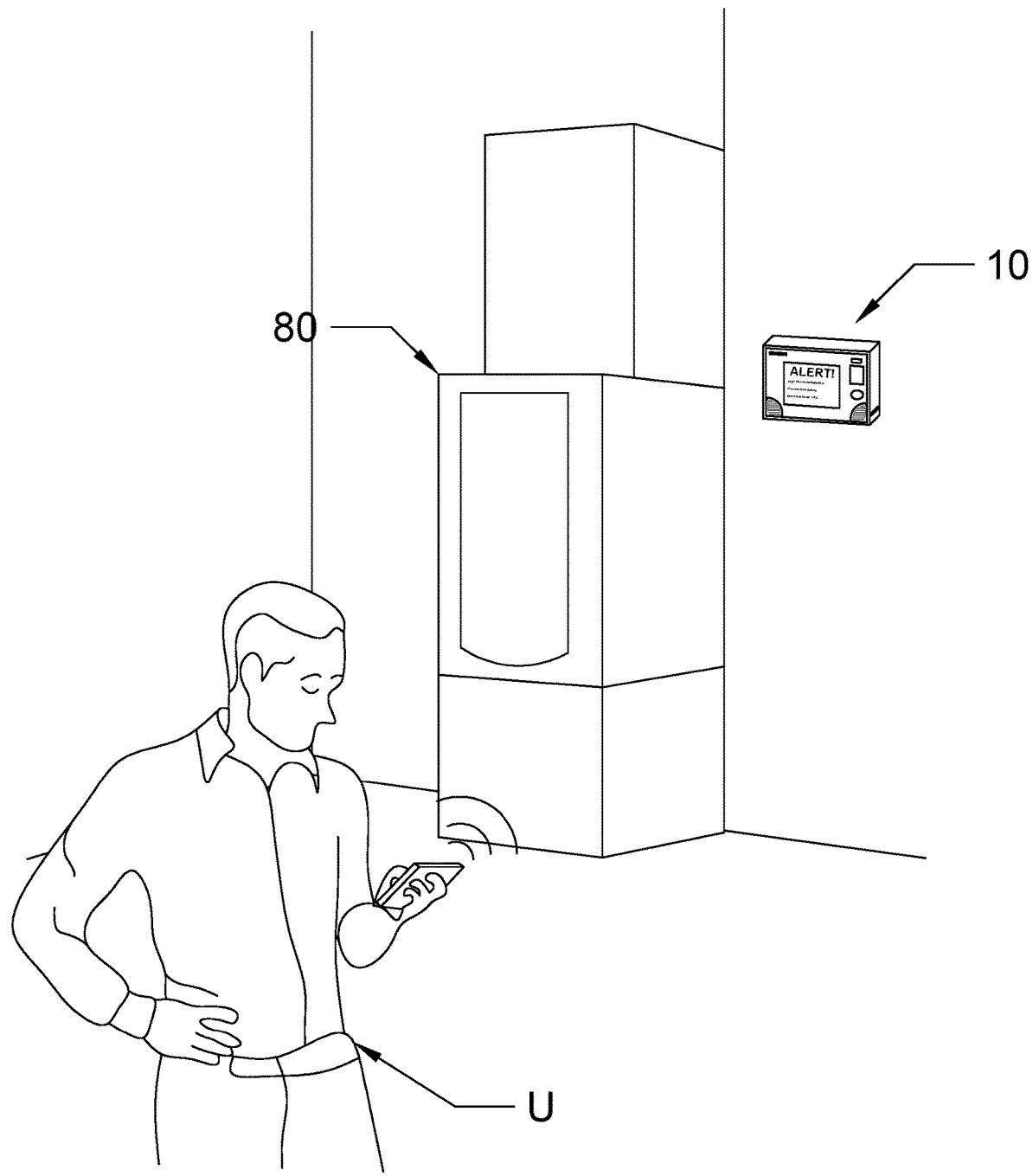
FIG. 1 represents an isometric operational view of the present invention 10 wherein a user U receives an alarm indicating that the CO levels are in dangerous levels.

Referring now to the drawings, where the present invention is generally referred to with numeral 10, it can be observed that it basically includes a sensor assembly 20, a shutoff assembly 40 and an alarm assembly 60. It should be understood there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

Figure 2:
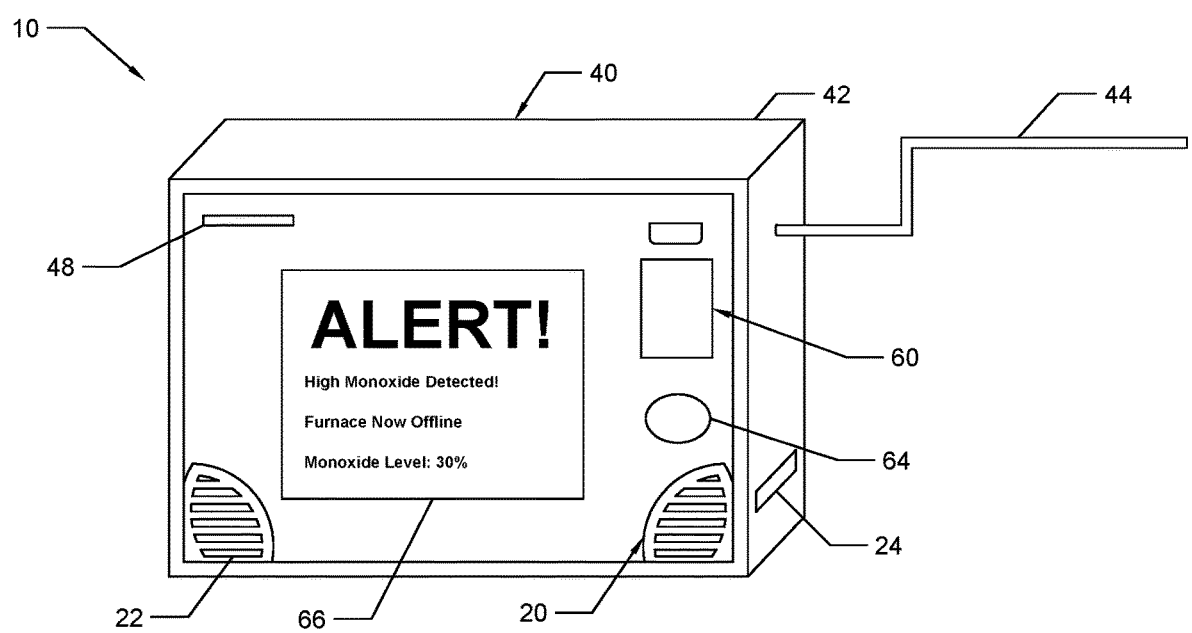
FIG. 2 shows an isometric view of the present invention 10. The present invention 10 includes a sensor assembly 20, a shutoff assembly 40 and an alarm assembly 60.
Figure 4:
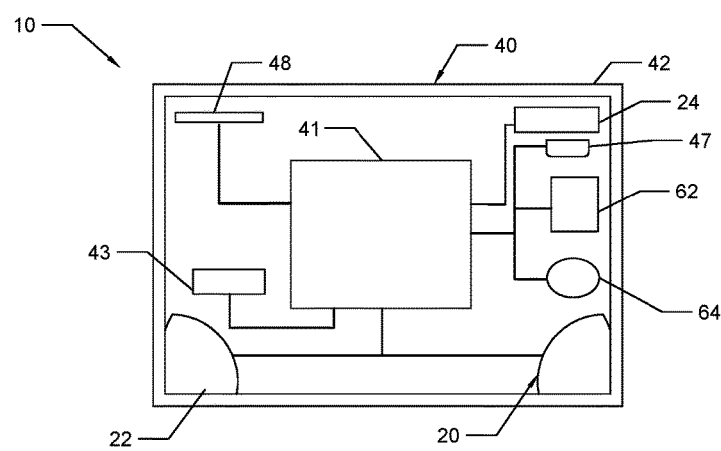
FIG. 4 is a representation of a diagram of the internal components of the shutoff assembly 40.

The sensor assembly 20 may include a plurality of sensors 22, at least one port 24 and a battery 26. As best illustrated in FIG. 2 and FIG. 4 the plurality of sensors may be located inside of the shutoff assembly 40. It also may be suitable for the plurality of sensors 22 to be located outside of the shutoff assembly 40. In an exemplary embodiment the plurality of sensors 22 may be located outside of the shutoff assembly 40 and be connected through at least one port 24. The plurality of sensors 22 may be located on different locations in a building.

It should be understood that the plurality of sensors 22 may be carbon monoxide (CO) sensors. The plurality of sensors 22 may be a biomimetic sensor, an electrochemical sensor, a metal oxide semiconductor, or any other carbon monoxide sensor known in the prior art. The plurality of sensors 22 may sense data of a carbon monoxide concentration level. The port 24 may be located on a right portion of the shutoff assembly 40. It also may be suitable for port 24 to have any other configuration in the shutoff assembly 40. The plurality of sensors 22 may be connected to a battery 22. The battery 22 may provide power to the plurality of sensors. It also may be suitable for the plurality of sensors 22 to be connected to a power outlet. The plurality of sensors 22 may be in communication with the shutoff assembly 40.

The shutoff assembly 40 may include a housing 42, storage 43, a microcontroller 41, transmitter 45 an actuator 47, a power cord 44 and a storage port 48. The housing 42 may have a rectangular shape. It also may be suitable for the housing 42 to have a circular shape, a cylindrical shape, or any other suitable shape. The housing 42 may be made of plastic, metal, or any other suitable material. The housing 42 may enclose the storage 43, the microcontroller 41, the transmitter 45 the actuator 47, the power cord 44 and the storage port. It also may be suitable for the housing 42 to enclose the sensor assembly 20 and the alarm assembly 60. The housing 42 may be hollow.

Figure 3:
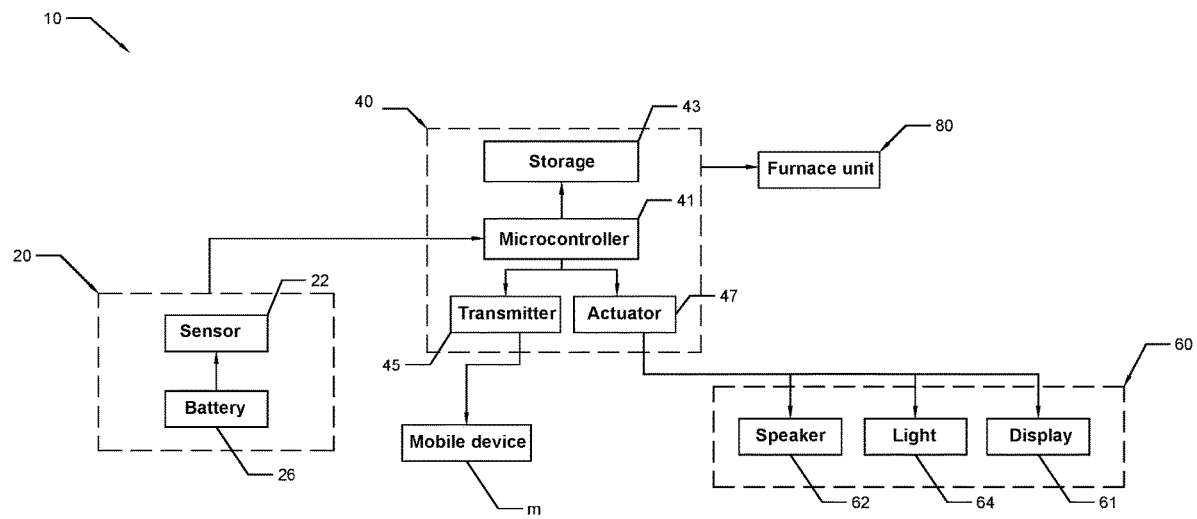
FIG. 3 illustrates a diagram of the sensor assembly 20 connected to the shutoff assembly 40 and the shutoff assembly 40 connected to the alarm assembly 60 and the furnace unit 80.

Referring now to FIG. 3 it can be observed that the plurality of sensors 22 may be connected to microcontroller 41. Thus, data of carbon monoxide concentration level detected by the sensor 22 may be transmitted to the microcontroller 41. The microcontroller 41 may identify if the carbon monoxide concentration level is high. If the carbon monoxide concentration level is high the microcontroller 41 may be actuated to shut off the furnace unit 80. A high level of carbon monoxide is normally any concentration greater than 101 PPM. The microcontroller 41 may be powered through the power cord 44. It also may be suitable for the microcontroller 41 to be powered through battery 26. Battery 26 may be a lithium battery, a carbon-zinc battery, or any other suitable battery.

The microcontroller 41 may control the transmitter 45. In an exemplary embodiment the microcontroller 41 may control the transmitter 45 to send a signal to a mobile device m if the carbon monoxide concentration level is greater than 101 PPM. The mobile device m may display an alert or emit a sound to indicate that the carbon monoxide concentration level is high. The transmitter 45 may preferably use Bluetooth technologies. It also may be suitable for the transmitter 45 to be used to send collected data from the plurality of sensors 22 to the mobile device m so the mobile device can store the collected data.

It also may be suitable to store the collected data from the plurality of sensors 22 through the storage 43. In an exemplary embodiment the storage 43 is a removable storage that can be inserted into storage port 48. Storage 43 may be a memory card, a pen drive or any other suitable storage known in the prior art.

The microcontroller 41 may be connected to actuator 41. The actuator 41 may be used to actuate the alarm assembly 60 to warn if the carbon monoxide concentration level is high. The shutoff assembly 40 may warn if the carbon monoxide concentration level is high through the transmitter 45 or through the actuator 47. The shutoff assembly 40 may be used to shut off the furnace unit 80 if carbon monoxide concentration level is high.

The alarm assembly 60 may include at least one speaker 62, at least one light 64 and a display 61. The at least one speaker 62 may be located on a front portion of the housing 42. It also may be suitable for the at least one speaker 62 to have any other configuration in the housing 42. In an alternative embodiment the speaker 62 may be placed separately from the housing 42. The at least one speaker 62 may emit a predetermined sound. The predetermined sound may indicate that carbon monoxide concentration level is high. The at least one light 64 may be located on a front portion of the housing 42. It also may be suitable for the at least one light 64 to have any other configuration in the housing 42. The at least one light 64 may preferably be a light emitting diode. The at least one light 64 may turn on if the carbon monoxide concentration level is high. The at least one light 64 may blink if the carbon monoxide concentration level is high.

The display 61 may also be located on a front wall of the housing 42. The display 61 may display the carbon monoxide concentration level. The display 61 may also display if the furnace unit 80 is on or off. The display 61 may also display the status of the plurality of sensors 22. The display 61 may further display an alert sign if the carbon monoxide concentration level is high. Display 61 may be located on a front wall of the housing 22. It also may be suitable for the display 61 to have any other configuration in the housing 42. The display 61 may be a liquid crystal display, a thin-film transistor, a light emitting diode display, or any other display known in the prior art. The display 61, the at least one speaker 62 and the at least one light 64 may be actuated through the actuator 47 to warn if the carbon monoxide concentration level is high.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A furnace shut off device, comprising:
a sensor assembly, the sensor assembly includes a plurality of sensors, wherein said plurality of sensors are carbon monoxide sensors, said sensors are configured to collect data of carbon monoxide concentration level;
a shutoff assembly, wherein said shutoff assembly includes a housing and a microcontroller, said housing has a rectangular shape, said microcontroller is inside said housing, said microcontroller is in communication with said plurality of sensors, said microcontroller is programmed to shut off a furnace unit if said carbon monoxide concentration level is greater than 101 parts per million; and
an alarm assembly, wherein said alarm assembly is in communication with said shutoff assembly, said alarm assembly includes at least one light, at least one speaker and a display, said at least one light, said at least one speaker, and said display being located on a front wall of said housing, wherein said at least one light is turned on if said carbon monoxide concentration level is greater than 101 parts per million, said speaker emits a predetermined sound if said carbon monoxide concentration level is greater than 101 parts per million, said display is configured to display a warning signal if said carbon monoxide concentration level is greater than 101 parts per million.

2. The furnace shut off device set forth in claim 1, wherein said plurality of sensors are inside said housing.

3. The furnace shut off device set forth in claim 1, wherein said plurality of sensors are connected to said shutoff assembly by means of a cord, wherein said cord is capable of being connected to a port in said housing.

4. The furnace shut off device set forth in claim 1, wherein said plurality of sensors are connected to a battery, said battery provides power to said plurality of sensors.

5. The furnace shut off device set forth in claim 1, wherein said shutoff assembly further includes a transmitter, said transmitter is adapted to transmit a warning signal to a mobile device.

6. The furnace shut off device set forth in claim 5, wherein said transmitter uses Bluetooth technologies.

7. The furnace shut off device set forth in claim 1, wherein said shutoff assembly includes an actuator, wherein said actuator actuates said speaker to sound, said actuator actuates said light to blink, said actuator is controlled by said microcontroller.

8. The furnace shut off device set forth in claim 1, wherein said display is adapted to display a first status for said plurality of sensors and a second status for said furnace unit, said first status is on or off, said second status is on or off.

9. The furnace shut off device set forth in claim 1, wherein said shutoff assembly includes storage, wherein said storage is capable of being used to store said collected data.

10. A furnace shut off device, comprising:
a sensor assembly, the sensor assembly includes a plurality of sensors, wherein said plurality of sensors are carbon monoxide sensors, said sensors are configured to collect data of carbon monoxide concentration level;
a shutoff assembly, wherein said shutoff assembly includes a housing, a transmitter, and a microcontroller, said housing having a rectangular shape, said microcontroller is inside said housing, said microcontroller is in communication with said plurality of sensors, said microcontroller is adapted to shut off a furnace unit if said carbon monoxide concentration level is greater than 101 parts per million, said transmitter is adapted to transmit a warning sign to a mobile device; and an alarm assembly, wherein said alarm assembly is in communication with said shutoff assembly, said alarm assembly includes at least one light, at least one speaker and a display, said at least one light, said at least one speaker, and said display being located on a front wall of said housing, wherein said at least one light is turned on if said carbon monoxide concentration level is greater than 101 parts per million, said speaker emits a predetermined sound if said carbon monoxide concentration level is greater than 101 parts per million, said display is configured to display a warning signal if said carbon monoxide concentration level is greater than 101 parts per million, wherein said display is adapted to display a first status for said plurality of sensors and a second status for said furnace unit, said first status is on or off, said second status is on or off.

11. A furnace shut off device, consisting of:

a sensor assembly, the sensor assembly includes a plurality of sensors, wherein said plurality of sensors are carbon monoxide sensors, said sensors are configured to collect data of carbon monoxide concentration level;

a shutoff assembly, wherein said shutoff assembly includes a housing, storage, a transmitter, and a microcontroller, said housing having a rectangular shape, said microcontroller is inside said housing, said microcontroller is in communication with said plurality of sensors, said microcontroller is adapted to shut off a furnace unit if said carbon monoxide concentration level is greater than 101 parts per million, said transmitter is adapted to transmit a warning sign to a mobile device, said transmitter uses Bluetooth technology, wherein said storage is capable of be used to store said collected data, wherein said plurality of sensors are inside of said housing, said plurality of sensors are connected to a battery, said microcontroller provides power to said plurality of sensors, said battery provides emergency power to said microcontroller; and an alarm assembly, wherein said alarm assembly is in communication with said shutoff assembly, said alarm assembly includes at least one light, at least one speaker and a display, said at least one light, said at least one speaker, and said display being located on a front wall of said housing, wherein said at least one light is turned on if said carbon monoxide concentration level is greater than 101 parts per million, said speaker emits a predetermined sound if said carbon monoxide concentration level is greater than 101 parts per million, said display is configured to display a warning signal if said carbon monoxide concentration level is greater than 101 parts per million, wherein said display is adapted to display a first status for said plurality of sensors and a second status for said furnace unit, said first status is on or off, said second status is on or off.

* * * * *